(12) United States Patent
Manderson

(10) Patent No.: US 6,712,073 B2
(45) Date of Patent: Mar. 30, 2004

(54) EXTRAMEDULLARY ROD IMPLANT FOR LONG BONES

(76) Inventor: Easton L. Manderson, 1750 Sir Galahad Way, Ashton, MD (US) 20861

(*) Notice: Subject to any disclaimer, the term of this patent is extended or adjusted under 35 U.S.C. 154(b) by 588 days.

(21) Appl. No.: 09/764,058

(22) Filed: Jan. 19, 2001

(65) Prior Publication Data
US 2001/0001821 A1 May 24, 2001

Related U.S. Application Data

(62) Division of application No. 09/343,180, filed on Jun. 30, 1999, and a division of application No. 08/494,678, filed on Jun. 26, 1995, now abandoned.

(51) Int. Cl.⁷ .......................... A61B 19/00; A61B 17/58
(52) U.S. Cl. ........................................ 128/898; 606/69
(58) Field of Search ............................. 606/60, 62, 69, 606/72, 61; 128/898

(56) References Cited

U.S. PATENT DOCUMENTS

| | | | | |
|---|---|---|---|---|
| 3,463,148 A | * | 8/1969 | Treace | 606/69 |
| 3,695,259 A | * | 10/1972 | Yost | 606/69 |
| 4,055,172 A | * | 10/1977 | Ender et al. | 606/62 |
| 4,573,458 A | * | 3/1986 | Glower | 606/69 |
| 4,630,601 A | * | 12/1986 | Harder et al. | 606/62 |
| 5,336,224 A | * | 8/1994 | Selman | 606/69 |
| 5,607,430 A | * | 3/1997 | Bailey et al. | 606/60 |

* cited by examiner

Primary Examiner—David J. Isabella
(74) Attorney, Agent, or Firm—Nigel L. Scott

(57) ABSTRACT

Described is a method of inserting a solid rod implant into the body. The implant is designed for bridging two portions of a broken long bone, united or ununited, and maintaining the divided portions of the bone in stable alignment with each other.

The solid rod implant is designed to be rigidly attached to the damaged long bone by means of a pair of partly tubular plates at either end of the rod. These plates provide the sole means of attachment of the implant to the bone i.e there is no provision for any attachments along, beside or through any portion of the rod that would allow it to be apposed to, or attached to any portion of the bone for which it is providing support for osteosynthesis. By its design and method of rigid attachment to the bone, through partly tubular end plates, the implant allows controlled motion at the fractured or non united portions of the bone fragments, a motion which stimulates rapidly forming external bridging callus formation for osteosynthesis of the long bone, a process that shortens the time of osteosynthesis of long bones so treated.

7 Claims, 5 Drawing Sheets

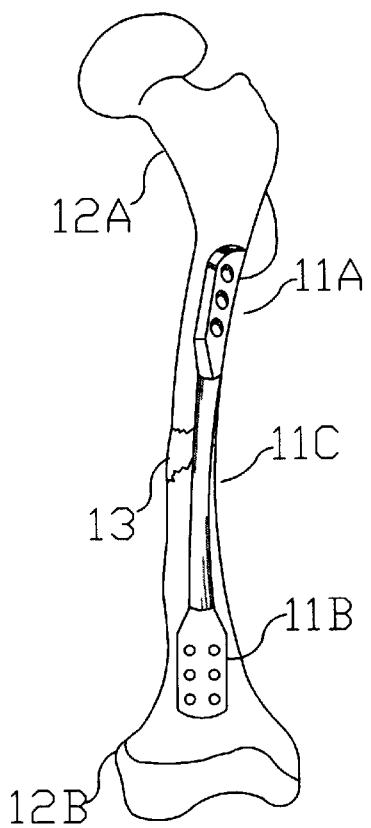
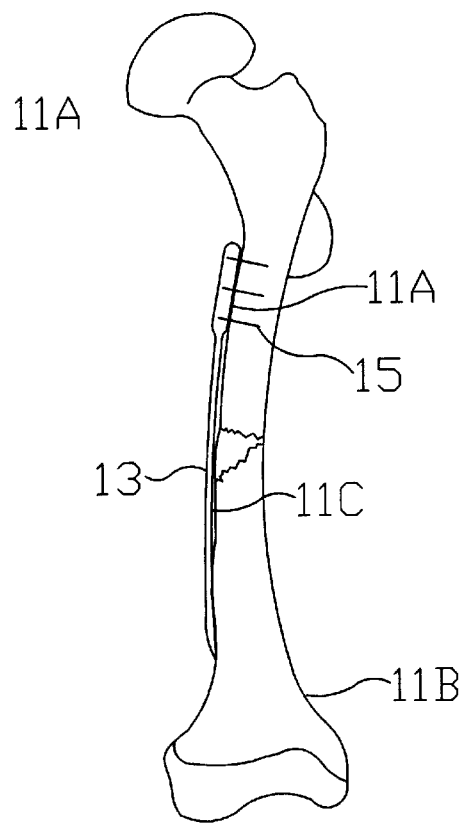
FIG. 2A
FIG. 2B

EXTRAMEDULLARY ROD IMPLANT FOR LONG BONES

CROSS REFERENCE TO RELATED APPLICATIONS

This application is a division of application Ser. No. 09/343,180, filed Jun. 30, 1999, for "Extramedullary Rod Fixateur for Bones" (now U.S. Pat. No. 6,488,685), which is a continuation-in-part of application Ser. No. 08/494,678, filed Jun. 26, 1995, for "Instrument for Osteosynthesis of Long Bone Fractures-Manderson Side Binder Implant" (now abandoned).

EXTRAMEDULLARY IMPLANT FOR LONG BONES

The present invention generally relates to a method of inserting an implant for internal stabilization and fixation of bone fragments to effect osteosynthesis of un-united bone fragments. The implant is particularly suitable for fractures of long bones, although it may be adaptable to bridge joints of long bones requiring arthrodesis or bones in a state of non union, malunion or pseudoarthrosis.

BACKGROUND OF THE INVENTION

It is well known in the art of bone fixation that the repair of fractured bones may be accomplished by the attachment of bone plates and intramedullary nails or rods to the injured bone to hold the fractured bone ends in place to foster healing. Bone plates and intramedullary rods or nails are designed to provide rigid fixation and support for applied loads while being subjected to cyclical loads in tension, compression, torsion and/or bending.

Bone plates are generally described as devices with at least one flattened surface, and with holes or grooves for screws and wires, respectively, situated in or along the main body of the plate, to allow fixation of the flattened surface of the device to the bone surface by means of screws or wires, for the purpose of holding the bone in place and achieving union of the bone fragments.

The bone plates traditionally are rigidly fixed to the bone to prevent motion between the fragments. Empirically, bone union occurs with rigid fixation, but rigid fixation of the bone fragments along significant lengths and breaths of the bone will weaken the bone through stress shielding and disuse atrophy. The adverse effects of stress shielding and disuse atrophy are prolonged healing time and refracture or discontinuity of the bone if the bone plate is removed after osteosynthesis.

Other adverse effects of plates are as follows: Healing also is generally without the formation and protective function of external callus; applying the plate for rigid fixation requires surgical dissection of the non-osseous tissues, a process which injures the external vascular and nutritional sources of the bone fragments and which may be imprudent in the presence of preceding traumatic injury to the bone and non osseous tissue.

Screw holes of plates are weak points or stress risers that may cause failure or breakage of the plate during load application especially if this load application is repetitive or cyclical. If a plate does not have fixation applied throughout its entire length, fixation may be inadequate for load support during load application which is usually in several planes, a situation that may result in loss of axial and rotational alignment, malunion or nonunion of the fragments and/or failure of the device along the stress rising, non-utilized screw holes. Needless to say, if several screw holes are left unused, then the remaining portion of the plate is usually not rigid enough to withstand cyclical applied loads without failure or deformation.

Generally, the loading configuration to which an implant is subjected is not limited to one particular plane. There may be simultaneous forces in several planes. If this is the case, cross sections which are asymmetrical may not be as satisfactory as those which are symmetrical for load bearing purposes. Thus, a plate which is usually flattened on one or more surfaces will not bear loads equally in all directions, and may be adequate to withstand forces in one direction but inadequate to withstand forces in another. By comparison, a round section device has equal properties for load distribution and bearing in all directions.

Intramedullary nails or rods are commonly used to support long bone fragments to effect osteosynthesis. The rod has several advantages over the plate. Placement can be subcutaneous at an entry point to the intramedullary canal of the long bone thereby avoiding surgical injury to the extra osseous tissues that provide nutritional and vascular support to the bone fragments especially in times of injury thereby lessening the risk of infection. Unlike plates, rods share functional loading in weight bearing during and after the osteosynthesis process thereby preventing disuse atrophy as seen with plate fixation for osteosynthesis. This feature makes a second operation for removal to allow functional load distribution to the bone often unnecessary. If removal is necessary, refracture of the bone is uncommon, unlike the case with removal of plates, because the functional capacity for load bearing returns to the bone during and after healing and before removal, since the rod shares function with the bone to which it is applied, thereby avoiding stress shielding of the bone.

For intramedullary osteosynthesis of long bones, the rod or nail may be rigid, flexible, circular, diamond shaped, rectangular, of open section or closed section. However, it has been proven that for a given cross sectional area, a closed circular configuration with symmetry in all directions is most reliable in sustaining forces applied in several planes.

The intramedullary rod or nail conventionally applied, has several disadvantages. Insertion technique has a steep learning curve and can be technically demanding and requires expensive and sophisticated equipment and well trained support personnel. Positioning of the patient must be precise to allow proper insertion and this is not always possible or practical for a seriously multiple injured or obese patient. The use of the intramedullary rod or nail is limited, almost precisely to treating the diaphyseal section of the long bone needing osteosynthesis.

Although axial alignment is usually assured with intramedullary rods or nails, rotational alignment is not assured unless the rod has a fluted end or unless the rod is locked proximally or distally with screws, a procedure that is difficult to do in the distal locking area. Because of the great difficulty in achieving precise screw placement, this step usually prolongs the operative time and time of exposure to radiation, consequently, intramedullary rodding or, nailing must be performed using fluoroscopy, to ensure precise placement.

SUMMARY OF THE INVENTION

In general, application of a strong, rigid rod for intramedullary placement for osteosynthesis of a long bone requires intramedullary reaming, a process that entirely destroys the inner ⅔ of the intramedullary vascular circulation to the diaphysis of the long bone. The outer ⅓ of the diaphysis is supplied by the external non osseous tissue. If this is also disrupted by injury at the time of reaming for nail or rod insertion then the undesirable situation of the diaphysis being completely without vascular supply exists making the bone fragments more susceptible to infection or the chances of union more unlikely.

If the rod is placed without reaming then the constraints of the intramedullary canal limits the diameter size of the rod or nail, a situation that may make it too thin and too flexible for effective load bearing or support as seen in cyclical weight bearing.

Moreover, after reduction of the fragments, the osteosynthetic device must be rigid enough to hold the fragments in the restored position and alignment during load application especially for the long bones of the lower extremity engaged in the cyclical load bearing of walking and for the long bones of the upper extremity engaged in cyclical load support as seen in crutch walking, for example.

The designer should make the device sufficiently rigid so as to provide no more than the maximal tolerable amount of relative motion during the healing process. Controlled motion at the non-united ends of the long bones is desirable to stimulate callus formation. The implant should also be rigid enough to withstand load sharing forces in all planes (compression, bending, twisting and tension), but not so rigid as to force the implant to continuously carry the load after healing has taken place since this situation would lead to fatigue failure of the implant. On the other hand, too much motion from a pliable or flexible rod could lead to a hypertrophic non-union in a long bone.

Considering the variation in anatomy and the biologic constraints on size of the implant, the ideal osteosynthetic implant is difficult to select by material selection criteria only. However, in selecting an ideal implant attention must be paid to factors including the combination of design, application, material selection, selection of cross sectional areas and lengths in broad categories such as small, medium and large. The implant should meet ideals of minimal soft tissue damage during application, rapid application with very limited amount and use of sophisticated equipment and personnel, load sharing with the bone fragments to which the implant is applied, before and after osteosynthesis. In addition, the implant will provide support for the rapid development of external callus driven by the stimulus of load sharing that causes controlled, benign motion at the un-united bone ends; rigidity and rigid fixation away from the bone ends that will allow controlled motion at the un-united bone ends while at the same time allowing load bearing and support, even of a cyclical nature. Further, the invention describes an implant for osteosynthesis that will initially bear the total load of the injured biologic structure, since the initial and basic purpose of this implant, should be to provide a means of load transmission across fractures or un-united bone fragments before synthesis has been achieved.

In accordance with applicant's invention, it is possible to overcome the many defects attributable to intramedullary rodding and extramedullary bone plate fixation through the use of an extramedullary rod which is capable of being rigidly attached to the extremities of a long bone, provide weight bearing support to the bone along its longitudinal axis and permit stimulatory forces of motion that generate callus repair at the point of nonunion of the bone. An extramedullary rod of this type is unknown to those skilled in the art.

OBJECTIVES OF THE INVENTION

A principal object of this invention is to provide rigid fixation of the bone fragments that will maintain axial and rotational alignment during load bearing of osteosynthesis.

Another object of this invention is to provide a bone implant that is pre-shaped to accommodate the general anatomy of the bone fragments to which it is applied and restore normal or near normal axial and rotational alignment of the bone after union.

Yet another object of the invention is to allow functional load sharing throughout fixation before osteosynthesis and after osteosynthesis.

A further object of the invention is for the implant to be applied in a rigid manner to the bone fragments with minimal surgical damage to the soft tissues that are external and internal to the bone.

One more object of the invention is for it to be applied with little or no contact of the rod section to the bone fragments while still providing rigid support to the fragments for load bearing.

A final object of the invention is by design and application to provide a method that would allow beneficial motion at the un-united bone ends of long bones that will stimulate the formation of external bridging callus between the un-united bone ends.

BRIEF DESCRIPTION OF THE DRAWINGS

FIGS. 2(A) & 2(B) shows the implant in place on a fractured femur.

DETAILED DESCRIPTION OF THE INVENTION

Figure 1A:
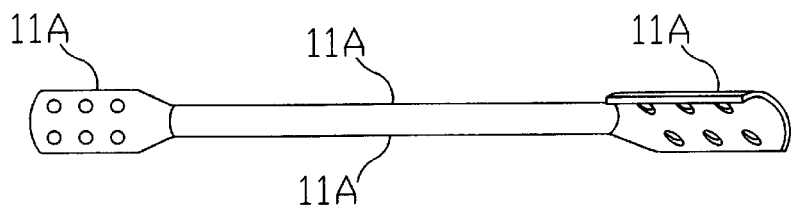
FIG. 1(A) is an enlarged longitudinal cross-sectional view of the implant present invention for fixation of a fractured femur showing the rod section, partially tubular end plates, screw holes and pedicles.
Figure 1B:
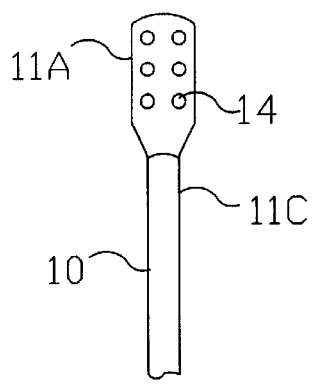
FIG. 1(B) is a surface view of the implant showing the partially tubular end plate and cylindrical rod section.
Figure 1C:
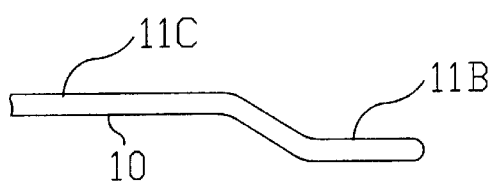
FIG. 1(C) is a lateral view of the implant showing the connection between cylindrical rod and tubular plates.
Figure 1D:
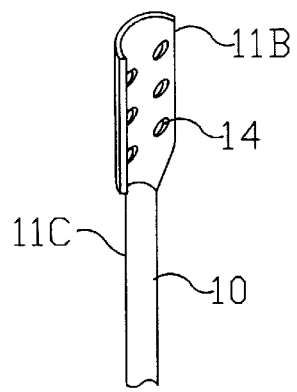
FIG. 1(D) is a profile underside of the implant showing the convex surface, cylindrical rod, and screw holes.
Figure 2:
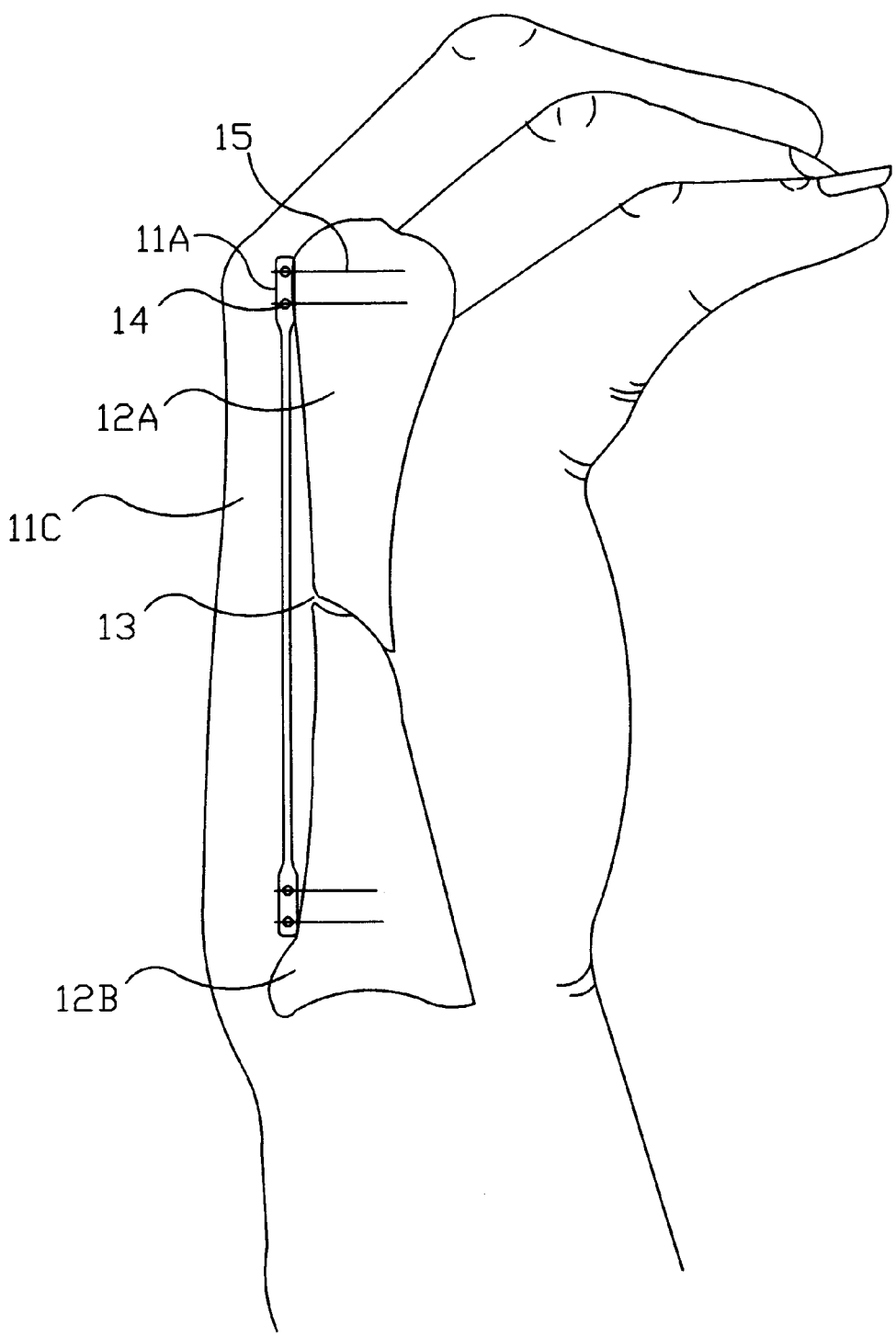
FIG. 2 shows the implant in position for the repair of a fractured phalangeal bone.
Figure 3A:
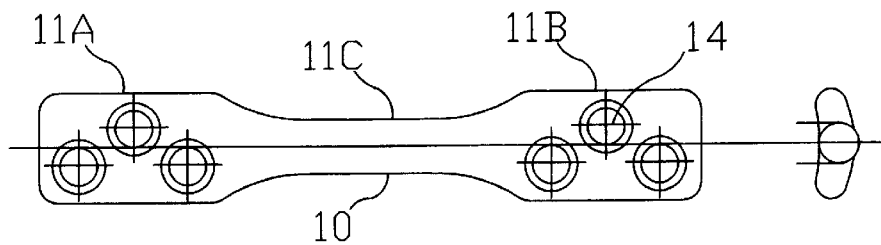
FIGS. 3(A), 3(B), 3(C) show different sizes of the implant for use in the repair of fractures of the ulnar, radial and wrist bones respectively.
Figure 3B:
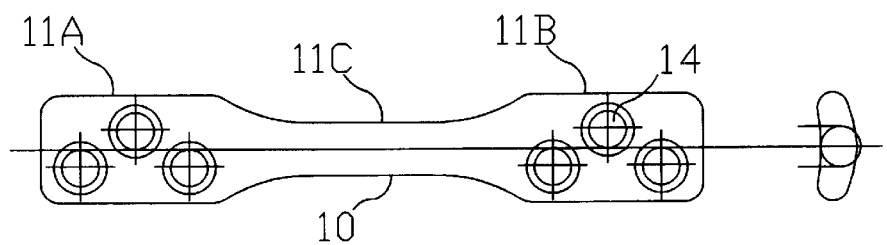
Figure 3C:
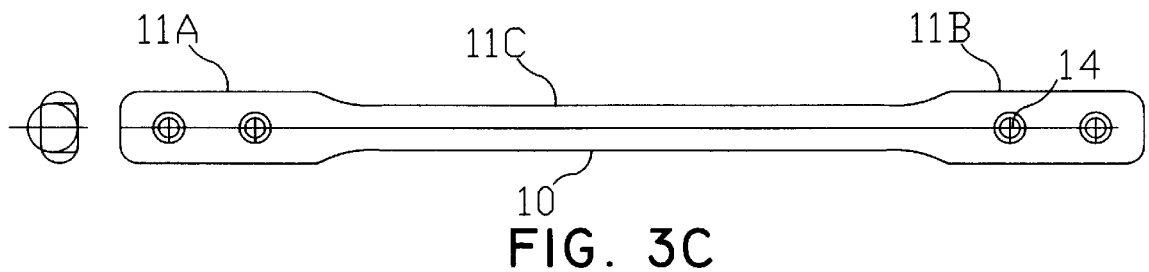
Figure 4A:
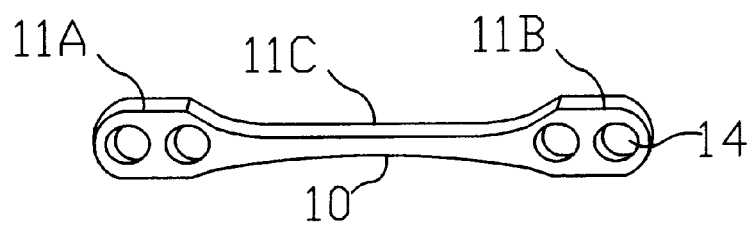
FIGS. 4(A), 4(B), 4(C) show different sizes of the implant for use on the phalangeal bone.
Figure 4B:
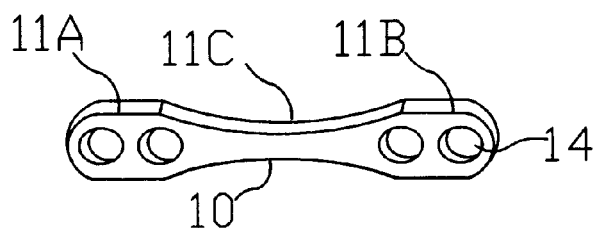
Figure 4C:

Referring to FIGS. 1A–1D there is shown a implant having the numeral 10 made of a rigid inert material, such as stainless steel. The implant 10 includes two identical substantially flat partially tubular end plates, 11A and 11B, with screw holes 14; and a middle rod section, 11C which joins the end plates, 11A and 11B. FIGS. 2A and 2B show the implant in place on a fractured femur 12, it will be noted that the middle rod section, 11C of the device is placed parallel and contiguous to the fractured bone, but is not fixed or attached to the ununited bone fragments 13, of the femur 12. The partially tubular ends of the implant are attached to the distal and proximal sections of the injured bone, 12A and 12B by means of screws 15. In addition, the inside curved surface of the implant is equipped with pedicles to facilitate the rigid non-continuous fixation of the implant to the bone.

Referring specifically to FIGS. 2A and 2B it can be seen that in practice the implant 10 is held in place on the fractured bone at the extremities of the bone, only and that the implant is completely unattached to the fractured bone except by means of tubular end plates which are attached to the proximal and distal ends of the injured bone. Generally, however, each tubular end plate is designed to accommodate up to five screw holes 14. The rod 11, portion of the implant spans the fractured area so that no screws or fixation devices are close to the fracture zone. This spanning feature, in turn, allows rigid fixation of the instrument at the ends while leaving the central portion of the bone unaffected by the presence of the implant. This unique method of fixedly attaching the instrument to the extremities of the bone, only, generates micro-motion at the ununited bone ends that encourages and sustains the more rapid healing due to external bridging callus formation, rather than the healing by the slower primary bone healing seen with rigid fixation. Since no dissection is done in the fractured area, and since the device is fitted extramedullarily, there is no disturbance of the endosteal blood supply (inner ⅔ of the cortex) or the periosteal blood supply (outer ⅓ of the cortex).

As shown from the FIGS. 2, 3A, 3B, 3C, 4A, 4B, and 4C, the implant of this invention, 10 is designed in form and manner to fit on any of the long bones of the body, including the thigh, leg, arm, forearm, hand, foot and wrist. Each implant will have a minor adjustment in form, shape or length to make it adaptable for the particular bone and the injured person.

One and the same femoral "side binder," for fractures of the femur (thigh), as designed, may be applied to the left or the right by reversing the ends, and may vary in lengths from approximately 10 inches to 13 inches.

The tibial "side binder" with respect to the treatment of fractures of the tibia (leg) is approximately 10 inches to 11 inches and because of the 90° axial rotation in the cylindrical portion is made in right and left models.

The Humeral "side binder," for fractures of the humerus (arm) comes in two lengths, one approximately 9 inches, and the other 10 inches, and because of the 90° axial rotation in the cylindrical portion is made in right and left models.

(Forearm) the Radial "side binder," for fractures of the radius and (forearm) ulnar "side binder," for fractures of the ulnar are one size, only and the length is determined accordingly.

The Wrist spanner, for fractures of the radius at the wrist is one size only and has four holes, two in each tubular end plate.

The implant is designed to be implanted quickly and with minimum disturbance of the surrounding bone and tissue to facilitate early bone healing. Moving the plate sections away from the fracture zone, as this implant does, decreases the rigidity of the fixation and allows for the maintenance of a stable but flexible environment in the region of the fracture. The flexibility also allows bending stress to be transmitted to the bone thereby preventing stress shielding. Further, because there are no stress rising holes in the spanning rod section, these implants can withstand cyclic loading such as crutch walking for the humerus and weight bearing for the femur and tibia, without the need for additional external fixation or support.

According to the procedure of this invention, some of the processes and techniques of intramedullary rod fixation are incorporated with those employed in extramedullary plate fixation to achieve results which have not been achieved previously.

In its preferred embodiment the implant is designed to treat femoral shaft fractures. The implant which is used in connection with treatment of a femoral shaft fracture is designed with anterior and lateral curves and its length will coincide with the length of the femur being repaired. The essential modifier in length selection is the length needed to span the fracture and injury site since surgical plate application should be well away from the fracture zone. The cylindrical section of the implant may vary in diameter from 10 to 12 millimeters to correspond to the size and weight of the injured person.

The length and diameter of the nail selected for fixation of the implant to the non-fractured bone ends may be modified according to patient size (length of femur), patient age (presence of growth plate), fracture grade (extent of comminution) and fracture pattern (transverse, oblique, spiral). Fixation may be accomplished by means of screws, nails or wire. If screws are used the type of screw may vary in length, diameter or screw type, depending on the nature of the fracture, the advantages to be gained by using one type of screw over another and the overall needs of the patient. In general, the diameter of the screws may be selected from among the following: 2.7, 3.5, 4.5, 6.5, 7.0 millimeters.

In fixing the femur, for example, and considering these factors the appropriate length of the implant can thus be selected by aligning the non-sterile implant on the extremity during restoration of femur length and orientation under fluoroscopy or on the non-injured thigh at the time of surgery, or plain radiographs of the injured or non-injured thigh preoperatively or intra-operatively.

In order to insert the instrument on a fractured femur, place patient supine or lateral on the fracture table and use fluoroscopy or plain radiographic equipment to restore anatomic length and orientation to the injured femur. Make two mid-lateral incisions, one distal and one proximal to the fracture zone in the thigh of the injured femur. The incised areas are connected by means of a sub-muscular tunnel through which the implant is inserted with the curve anterior. Hold the plate sections to the lateral cortices temporarily by placing Steinman pins through a plate hole in the distal and proximal end plates. To fix the plate permanently to the bone, place at least three screws in each plate section, depending upon the length of the femur and the size of the patient.

For supracondylar fractures of the femur, 6.5 mm cancellous screws can be used in the distal metaphyseal fragment. If the bone is osteoporotic, the fixation can be augmented with bone cement. Proper rotation of the femur will usually be ensured with identical lateral placement of the plate sections. The wounds should be copiously irrigated with antibiotic solution and closed in layers in the usual fashion. Closed suction drainage is optional if proper hemostasis has been achieved. Apply sterile dressing and discontinue traction, if used preoperatively.

Postoperatively, the patient may sit up in chair or get out of bed as general condition allows. Continue appropriate broad spectrum antibiotics started preoperatively and continue for 24–48 hrs, postoperatively. Physical therapy is indicated for upper and lower extremity strengthening and ambulation training is begun as soon as general condition allows with partial weight bearing for the affected extremity until bridging mature callus formation is seen radiographically, then full weight bearing is recommended.

Removal of the implant is optional. If removed, as per clinical situation or surgeon's choice after mature healing, the extremity should be protected with partial weight bearing and crutches or other walking aid for a period of at least six weeks.

The cylindrical rod implant is attached to the bone segments by plates at its ends rather than its sides and offset in such a manner that would allow it to provide little or no contact with any bone surface along which it traverses.

Each plate would contain at least 2 holes for 2 screws of appropriate sizes for small long bones and between 3 and 5 screw holes for fixation to large long bones of the extremities of appropriate sizes for long bones such as the humerus in the upper extremity and the tibia and femur in the lower extremity.

For long bones such as the humerus in the upper extremity and the tibia in the lower extremity, a pre-designed built-in 90° rotation of the rod would be available to allow the plate sections to be attached to the proximal lateral metaphyseal areas proximally, and the distal anterior metaphyseal areas distally, simultaneously, which after length is restored by reduction techniques will assure restoration of correct rotational alignment.

Because of the 90° rotation of the rod used for stabilization of the humerus or the tibia, the partially tubular plates are oriented to each other, so that when the plates are attached to the injured bone laterally, proximally and anteriorly distally the natural alignment and rotational orientation of the bone is restored.

The rod may be made of suitable naturally occurring or man made material, including stainless steel, titanium or other presently known or unknown materials to be implanted in biological tissues of animals such as humans. If the rod is made of certified stainless steel or other such suitable material, and designed for an upper extremity long bone such as the humerus, and for lower extremity long bones such as the femur and tibia, an implant of appropriate rigidity and thickness must be selected. An internal rod implant for use on the long bones such as the humerus, femur, tibia should be designed to allow cyclical weight bearing of up to ½ the body weight immediately after application in order to allow controlled motion at the fracture site or ununited ends of the bone, to stimulate the formation of external bridging callus and up to full body weight once radiographs reveal external bridging callus.

This controlled motion at the site of the fracture or nonunion is effected by attaching the rigid rod subcutaneously through the attached plate sections only, to the bone fragments at or near the metaphyseal areas of the long bone fragments, away from the injured soft or bone tissues or areas of non-union of the bone fragments and encouraging loading of the bone fragments by weight bearing or active motion of the involved extremity. This is in direct contrast to conventional application of plates through direct approach to the injured bone area and soft tissue with application of the plate along a flat or contoured surface directly to the bone surface in and around the area of the fracture or nonunion and beyond the area of the fracture or non-union, a process that injuries the soft tissue and shields the bone from loading forces, thereby causing bone atrophy while preventing bridging, external callus formation.

Although those skilled in the art of osteosynthesis can appreciate that at times incising the skin in the area of the fracture or non-union is necessary to clean or debride unwanted tissue, the design and intent of application of this implant is to apply it in such a way that its application will do little or no harm to the bone or non-osseous tissue in the region needing care and osteosynthesis; to apply it in such a manner that it will allow the natural physiologic healing process of callus formation and bridging of the bone fragments to be stimulated and enhanced; to apply it in such a manner that it will allow cyclical weight bearing of the extremity in which it is placed without permitting loss of the fixation, deformity of the bone fragments or failure of the implant through breaking, buckling or bending. The design and application therefore, are integral features of a system designed to promote healing by peripheral callus formation.

Therefore, to accomplish the above, the implant is inserted subcutaneously and atraumatically through an incision that is proximal or distal to the area of injury or nonunion, harvested through an incision that is proximal or distal to the area of injury or nonunion after passing atraumatically across the area of injury or non-union and rigidly fixed to or near the vascular and healthy metaphyseal areas of the long bone fragments.

Because the rod section of the implant which is continuous with the partly tubular plates is offset from the plate to lie in a different plane that is superior to the plane of the plate relative to the bone fragments, the rod lies away from the surface of the bone fragments to which the plates are attached, is not affixed to the bone surface or non osseous tissue, and because of its offset posture relative to the plate has little or no contact with the bone, a desirable feature that prevents contact injury to osseous or non osseous tissue and prevents disuse atrophy of the bone while providing support of the bone fragments and stimulation for callus formation.

The design of the end plates is critical to the function of the implant. On its outer surface, that is, the surface removed from attachment to the bone, the instrument is generally flat. On the other hand, the inside surface for attachment to the bone has a distinctive curvature to coincide with the generally curved surface of the bone to which it is to be attached. In addition, the inside surface of the instrument has pedicles to facilitate the rigid non-continuous attachment of the tubular plates to the bone. In addition, since the rod section of the implant has no protruding plate or other means of fixedly attaching the rod section to the bone, the rigidity of the attachment of the ends of the instrument to the bone is very important to the functioning of the device.

The foregoing is illustrative of the broad uses of the invention, however, it is not intended that all possible variations of the invention known to those skilled in the art have been included in this description.

What I claim is:

1. A method of stabilizing and repairing a fractured long bone, comprising, selecting an extramedullary implant of appropriate length for restoring said bone to its pre-fracture length, making a pair of incisions in the skin at the non-fracture bone ends proximally and distally of the fracture site, creating a sub-muscular passageway equal in length to the length of the distance between said incisions, inserting said implant through said incisions into said passageway and positioning said implant to lie in parallel alignment with said fractured bone, and affixing the proximal and distal ends of said implant to the proximal and distal non-fractured extremities of said bone.

2. The method of repairing a fractured long bone as claimed in claim 1 including securing said implant to said non-fracture bone extremities by screw, wire or other suitable fasteners.

3. The method of repairing a fractured long bone as claimed in claim 1 wherein the pre-fracture length of said fractured bone is determined by fluoroscopyy or plain radiographs.

4. The method of repairing a fractured long bone as claimed in claim 1 wherein said implant is a solid, elongated cylindrical rod.

5. The method of repairing a fractured long bone as claimed in claim 4 including selecting the length, diameter and rotational alignment of said rod relative to the fractured bone to be repaired, the medical condition of the patient and the particular long bone to be repaired.

6. A method of internal fixation of fractured bone fragments comprising:

selecting a solid, elongated, cylindrical rod implant having partly tubular end plates, making a pair incisions in the skin at the proximal and distal non-fracture ends of the bone fragments in identical lateral locations, creating a sub-muscular passageway parallel to said fractured bone fragments to connect said proximal and distal incisions, determining the prefracture length of said fractured bone by passing said implant through said incisions and placing said implant in said sub-muscular passageway oriented to the lateral and anterior aspects of the tibia and humerus, use of fluoroscopy or plain radiographs, and selecting an implant of approximate length, diameter and rotational alignment to restore said fractured bone to its pre-fracture length, alignment and rotation, affixing said tubular plates of said implant to said proximal and distal ends of said fractured bone using screws or other suitable means of fastening said plate to said fractured bone to maintain said bone fragments in stable alignment and rotation.

7. A method of effecting osteosynthesis of ununited bone fragments comprising:

selecting a solid, elongated, cylindrical rod implant having partly tubular end plates, making a pair incisions in the skin at the proximal and distal ends of the bone fragments in identical lateral locations, creating a sub-muscular passageway parallel to said fractured bone fragments to connect said proximal and distal incisions, determining the pre-fracture length of said fractured bone by use of fluoroscopy or plain radiographs, and selecting an implant of appropriate length, diameter and rotational alignment to restore said fractured bone to its pre-fracture length, alignment and rotation, passing said implant through said incisions and placing said implant in said sub-muscular passageway so that the curve of said implant is oriented to the lateral and anterior aspects of the tibia and humerus, affixing said tubular plates of said implant to said proximal and distal ends of said fractured bone using screws or other suitable means of fastening said plate to said fractured bone to maintain said bone fragments in stable alignment and rotation.

\* \* \* \* \*